United States Patent [19]

Lavanish et al.

[11] Patent Number: 4,911,749

[45] Date of Patent: Mar. 27, 1990

[54] AQUATIC HERBICIDAL METHODS

[75] Inventors: Jerome M. Lavanish, Akron; Barry Van Gemert, Massillon, both of Ohio

[73] Assignee: American Cyanamid Company, Stamford, Conn.

[21] Appl. No.: 370,421

[22] Filed: Jun. 20, 1989

Related U.S. Application Data

[60] Division of Ser. No. 864,931, May 19, 1986, Pat. No. 4,857,099, which is a continuation of Ser. No. 626,916, Jul. 2, 1986, which is a continuation-in-part of Ser. No. 544,938, Oct. 24, 1983, abandoned, which is a division of Ser. No. 348,479, Feb. 12, 1982, Pat. No. 4,426,527.

[51] Int. Cl.$^4$ ............................................. A01N 21/00
[52] U.S. Cl. ......................................................... 71/92
[58] Field of Search ........................... 71/66, 67, 92, 88

[56] References Cited

U.S. PATENT DOCUMENTS 4,857,099 8/1989 Lavanish et al. ...................... 71/92

Primary Examiner—Richard L. Raymond
Assistant Examiner—Eric Kraus
Attorney, Agent, or Firm—Alice C. Brennan

[57] ABSTRACT

This invention concerns the use of certain 3-[5- or 3-substituted-1,2,4-oxadiazol-3- or -5-yl]-1-substituted -4-substituted-5-substituted or unsubstituted-2-imidazolidinones to control growth of terrestrial or aquatic plants.

4 Claims, No Drawings

AQUATIC HERBICIDAL METHODS

CROSS-REFERENCE TO RELATED APPLICATIONS

This is a division of application, Ser. No. 864,931, filed May 19, 1986, now U.S. Pat. No. 4,857,099 which is a continuation of application Ser. No. 626,916, filed July 2, 1986, which is a continuation-in-part of application Ser. No. 544,938, filed Oct. 24, 1983, now abandoned, which is a division of application Ser. No. 348,479, filed Feb. 12, 1982, now U.S. Pat. No. 4,426,527.

FIELD OF THE INVENTION

This invention concerns certain 3-[5- or 3-substituted-1,2,4-oxadiazol-3- or -5-yl]-1-substituted-4-substituted-5-substituted or unsubstituted-2-imidazolidinones having herbicidal activity and the use thereof to control terrestrial or aquatic vegetation.

DESCRIPTION OF THE INVENTION

This invention concerns methods for controlling undesirable terrestrial or aquatic vegetation. More particularly the invention is directed to methods for controlling the growth of undesirable terrestrial or aquatic plants by contacting the terrestrial or aquatic plants with a herbicidally effective amount of 3-[5- or 3-substituted-1,2,4-oxadiazol-3- or -5-yl]-1-substituted-4-substituted-5-substituted or unsubstituted-2-imidazolidinones represented by the formula:

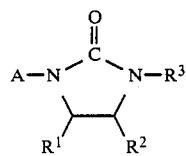

wherein:
A is

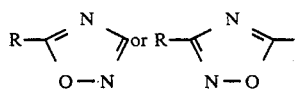

R is alkyl or haloalkyl of up to 6 carbon atoms, cycloalkyl of from 3 to 8 carbon atoms, alkenyl or alkynyl of up to 5 carbon atoms, —$R^4$—O—$R^5$ $R^4$—S—$R^5$ wherein $R^4$ is alkylene of up to 6 carbon atoms and $R^5$ is alkyl of up to 6 carbon atoms,

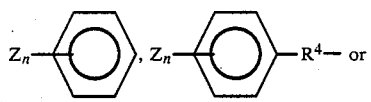

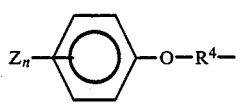

wherein Z is nitro, halogen, trifluoromethyl or $R^5$ and n is 0, 1, 2, or 3;
$R^1$ is hydroxy, halogen,

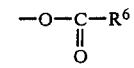

wherein $R^6$ is alkyl or haloalkyl of up to 6 carbon atoms, cycloalkyl of from 3 to 8 carbon atoms, alkenyl or alkynyl of up to 5 carbon atoms or

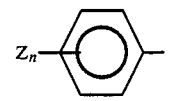

wherein $Z^1$ is nitro, halogen, trifluoromethyl, alkyl or alkoxy of up to 8 carbon atoms and n is 0, 1, 2 or 3 or

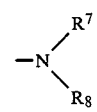

wherein $R^7$ and $R^8$ are the same or different and represent hydrogen, alkyl or haloalkyl of up to 6 carbon atoms; or $R_7$ can be

$R^2$ is hydrogen, hydroxy, alkyl, or haloalkyl of up to 4 carbon atoms or allyl; and
$R^3$ is alkyl of up to 3 carbon atoms or allyl.

Some alkyl groups of which the various constituents in the above formula are representative are, for example, methyl, ethyl, n-propyl, isopropyl, n-butyl, isobutyl, sec-butyl, pentyl, hexyl, or the like, including combinations thereof, e.g., 1,1-dimethylethyl. Exemplary alkoxy groups are methoxy, ethoxy, propoxy, butoxy, octoxy, and the like. As examples of cycloalkyl groups there may be mentioned cyclopropyl, cyclobutyl, cyclopentyl, cyclohexyl, cyclopentyl, and cyclooctyl. Allyl, butenyl, pentenyl, propynyl, butynyl, pentynyl and the like are exemplary of suitable alkenyl and alkynyl groups represented by the various constituents in the above formula. Representative suitable alkylene groups are, for example, methylene, ethylene, propylene, butylene, pentylene, or hexylene. As the halogen substituents, there may be mentioned chlorine, bromine, iodine, or fluorine, preferably chlorine or bromine.

Preferred compounds useful according to this invention are those wherein R and $R^3$ are alkyl, $R^1$ is hydroxy, $R^2$ is hydrogen or hydroxy and X is oxygen, some examples of which are 3-[5-(1,1-dimethylethyl)-1,2,4-oxadiazol-3-yl]-1-methyl-4-hydroxy-2-imidazolidinone, 3-5-(1,1-dimethylethyl)-1,2,4-oxadiazol-3-yl]-1-methyl-4,5-dihydroxy-2-imidazolidineoneand 3-[3-(1,1-dimethylethyl)-1,2,4-oxadiazol-5-yl]-1-methyl-4,5-dihydroxy-2-imidazolidinone. As exemplary of additional compounds believed to have herbicidal activity in accordance with this invention, there may be mentioned 3-[5-(1,1-dimethylethyl-1,2,4-oxadiazol-3-yl]-1-methyl-4-acetoxy-2-imidazolidinone,3-[5-(1.1-dimethylethyl)-1,2,4-oxadiazol-3-yl]-1-,ethyl-4-benzoyloxy-2-imidazolidinone and 3-[5-(1,1-dimethylethyl)-1,2,4-oxadiazol-3-yl]-1-methyl-4-butyryloxy-2-imidazolidinone.

Useful compounds of this invention of the 3-yl series wherein $R^1$ is hydroxy and $R^2$ is other than hydroxy, e.g., hydrogen, may be conveniently be prepared by reacting, in a first step, an appropriately substituted carbonyl chloride of the formula R—COCl, where R is as previously defined with cyanamide to prepare a compound of the formula R—CO—NHCN. This reaction is typically conducted in a cold, alkaline reaction medium the reaction product being crystallized by treatment of the reaction mixture with a cold, dilute aqueous acidic salt solution, e.g., dilute aqueous hydrochloric acid saturated with sodium chloride.

In a second step, the isolated reaction product from step one is reacted with hydroxylamine hydrochloride in the presence of an acid acceptor to prepare the corresponding 3-amino-5-(substituted)-1,2,4-oxadiazole of the formula:

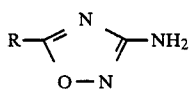

Useful compounds of the 5-yl series may be prepared by reaction of an appropriate nitrile of the formula R—CN where R is as previously defined, with an alcohol and hydrogen chloride, followed by reaction with cyanamide and then with hydroxylamine as described by K. R. Huffman and F. C. Schaefer, J. Org. Chem. 28, 1816 (1963) to give the corresponding 5-amino-3-(substituted)-1,2,4-oxadiazole of the formula:

The isoxazolamine is then phosgenated to the correspong isocyanate of the formula A—NCO wherein A is as previously defined. The isoxyanate is then reacted in a third step, with an appropriately substituted amino acetaldehyde dialkyl acetal of the formula $R^3$—N-H—CH($R^2$)CH($OR^9$)$_2$, wherein $R^2$ and $R^3$ are as previously defined and $R^9$ is alkyl of up to 6 carbon atomns or —CH($OR^9$) forms a 5 to 6 membered heterocyclic ring which may contain up to 3 hereto atoms to form an acetal urea of the formula:

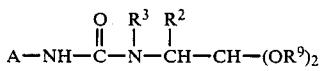

In the final step the acetal urea is hydrolyzed by heating in a dilute aqueous acid medium, e.g., hydrochloric acid, to form a compound of the invention wherein $R^1$ is hydroxy.

If it is desired to prepare a compound useful according to the invention wherein both $R^1$ and $R^2$ are hydroxy, a 3- or 5-amino-3- or 5-(substituted)-1,2,4 oxadiazol (prepared as described previously) is reacted with an appropriately substituted isocyanate of the formula $R^3$—N=C=O, wherein $R^3$ is a as previously defined to form a urea of the formula A— N(H)— C(O-)—N($R^3$)—H which is reacted with glyoxal to form a compound useful according to the invention having a hydroxy substituent in both the $R^1$ and $R^2$ positions.

A useful compound of the invention wherein $R^1$ is halogen, e.g., chlorine or bromine, may be prepared by reacting a compound of the invention of the formula:

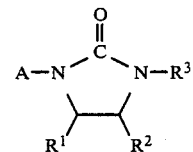

wherein A, $R^2$ and $R^3$ are as previously defined with a suitable halogenating agent typically in the presence of an inert solvent and optionally in the presence of an acid binding agent. When it is is desired to halogenate useful compounds of the invention wherein both $R^1$ and $R^2$ are hydroxy, it is necessary to protect the hydroxy group at the $R^2$ position by, for example, alkylation followed by removal of the alkyl group subsequent to halogenation.

To prepare a useful compound of the invention wherein $R^1$ is

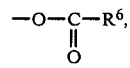

a compound of the invention having the formula:

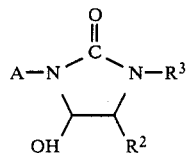

is reacted with an anhydride of the formula:

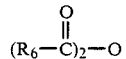

wherein A, $R^2$, $R^3$ and $R^6$ areas previously defined. This reaction is typically conducted at reflux temperature in the presence of an acid acceptor such as triethylamine, pyridine, N,N-dimethylaniline or the like and in the presence of an inert solvent such as benzene, methylene chloride, chloroform, ethyl acetate, tetrahydrofuran or the like.

It is, of course, to be realized that all of the above-described modes of preparation employ well-known analytic techniques and that any useful compound within the scope of the invention may readily be prepared by one skilled in the art using the same or similar methods. Synthesis of a specific compound useful according to this invention is illustrated by the following Example:

EXAMPLE I

Preparation of 3-[5-(1,1-dimethylethyl)-1,2,4-oxadiazol-3-yl]-1-methyl-4-hydroxy-2-imidazolidinone (a) To a flask provided with a magnetic stirrer was charged 160 milliliters of 10 percent aqueous sodium hydroxide and 34 grams of a 50 percent aqueous cyanamide solution. The flask contents were maintained at a temperature in the range of 0° to 5° C. by immersion in a salt and ice bath. To the cold solution was added dropwise, with contact stirring, 50 milliliters (0.4 mole) of trimethylacetyl chloride. After addition of about 0.2 mole of trimethylacetyl chloride, sufficient additional aqueous sodium hydroxide solution was added to maintain a pH of about 10. The reaction mixture was stirred in the ice bath for one-half hour, after which the ice bath was removed and stirring was continued for an additional one-half hour. Cold dilute aqueous hydrochloric acid saturated with sodium chloride was then added until the mixture turned milky and crystal formation was observed. The crystalline material was separated by filtration, suction dried and dried in a vacuum oven yielding about 40 grams of dried material.

(b) The crystalline material prepared in paragraph (a) of this Example was added incrementally, with stirring, to a mixture of 25 grams of hydroxylamine hydrochloride in 125 milliliters of pyridine, the temperature of the reaction mixture being maintained below 40° C. A mild exotherm was observed. After addition was complete, the reaction mixture was stirred over the weekend at ambient temperature. The reaction mixture was then diluted with 100 milliliters of water and 100 milliliters of 30 percent aqueous sodium hydroxide, the latter added in four increments. After phase separation, the organic layer was removed and concentrated on a rotary evaporator to remove pyridine leaving an oily residue which crystallized upon addition of saturated aqueous sodium chloride. A total of 24.77 grams of crystals melting at 81° to 83° C. were obtained.

(c) To a 500 milliliter flask provided with a paddle stirrer, a gas inlet tube, and a dry ice condenser fitted with a drying tube was charged 20 grams of the crystalline material prepared in paragraph (b) of this Example dissolved in 400 milliliters of toluene. Dry hydrogen chloride gas was added resulting in the formation of a voluminous precipitate after which phosgene was bubbled in below the liquid surface resulting in dissolution of most of the precipitate. The reaction mixture was stirred overnight at ambient temperature and then gently warmed to remove excess phosgene. Considerable frothing was observed until the temperature reached about 70° C. The flask was then purged with nitrogen at a temperature of 70° to 80° C. for about 8 hours after which heating was discontinued and nitrogen purging continued overnight. The mixture was stripped on a rotary evaporator to remove toluene leaving a white-yellow solid. The solid was placed in a vacuum oven at moderate heat. When sublimation of the solid was noted, the solid was removed from the oven, 20 grams of solid material being obtained.

(d) To a flask provided with reflux condenser and magnetic stirring bar was charged 3.14 grams of the solid material prepared as described in paragraph (c) of this Example dissolved in 75 milliliters of toluene and 2.4 grams of methylamino acetaldehyde dimethylacetal. The mixture was stirred for one hour at ambient temperature and then slowly heated to just below reflux temperature and maintained at this temperature, with stirring overnight. The mixture was then cooled, filtered and stripped on a rotary evaporator to remove toluene leaving an oily residue. The oil residue was then stirred vigorously with 75 milliliters of water containing 0.75 milliliter of concentrated sulfuric acid. The mixture was then gradually heated, with stirring, to 80° C. and maintained at this temperature for one-half hour, most of the oil going into solution. The reaction mixture was then filtered to remove undissolved oil and the clear aqueous solution was extracted with two 75-milliliter portions of chloroform. The combined chloroform extracts were concentrated on a rotary evaporator leaving an oily residue which crystallized upon cooling and addition of a small amount of diethyl ether. After filtration and washing with diethyl ether, 1.5 grams of crystalline product were obtained melting at 125° to 129° C., and identified by mass spectrum and NMR analyses as 3-[5-(1,1-dimethylethyl)-1,2,4-oxadiazol-3-yl]-1-methyl-4-hydroxy-2-imidazolidinone.

The mode of synthesis of a specific compound useful according to this invention has been illustrated by the foregoing Example; but it is to be understood that any compound contemplated within the scope of this invention may be prepared by those skilled in the art simply by varying the choice of starting materials and using the illustrated techniques or other suitable techniques.

The compounds of this invention are believed effective in regulating the growth of a variety of undesirable terrestrial plants, i.e., weeds, when applied, in an herbicidally effective amount, to the growth medium, i.e., the soil, prior to emergence of the weeds or to the weeds subsequent to emergence from the growth medium.

The term "herbicidally effective amount" is that amount of a compound of this invention required to so injure or damage weeds such that the weeds are incapable of recovering following application. It is, of course, understood that the compound, in addition to providing satisfactory weed control, must not cause significant damage to any crop amongst which the weeds are growing. The quantity of a compound of this invention applied in order to exhibit a satisfactory herbicidal effect may vary over a wide range and depends on a variety of factors, such as, for example, hardiness of a particular weeds species, extent of weed infestation, climatic conditions, soil conditions, method of application, and the like. Typically, as little as 0.2 or less pound per acre of a compound of this invention would be expected to provide satisfactory weed control, although in some instances application rates in excess of one pound per acre; e.g., up to 5 or more pounds per acre might be required. Of course, the efficacy of a particular compound against a particular weed species may readily be determined by routine laboratory or field testing in a manner well known to the art. It is expected that satisfactory weed control can be had at a rate of application in the range of 0.01 to 1.0 pound per acre.

Of course, a compound of this invention can be formulated according to routine methods with any of several known and commonly used herbicidal diluents, adjuvants and carriers. The formulations can contain liquid carriers and adjuvants such as organic solvents, as well as emulsifiers, stabilizers, dispersants, suspending agents, spreaders, penetrants, wetting agents and the like. Typical carriers utilized in dry formulations include clay, talc, diatomaceous earth, silica and the like. Preferred formulations are those in the form of wettable powders, flowables, dispersible granulates or aqueous emulsifiable concentrates which can be diluted with water at the site of application. Also, dry formulations such as granules, dusts, and the like, may be used.

When desired, a compound of this invention can be applied in combination with other herbicidal agents in an effort to achieve even broader vegetative control. Typical herbicides which can be conveniently combined with Formula I compound include atrazine, hexazinone, metribuzin, ametryn, cyanazine, cyprazine, prometon, prometryn, propazine, simazine, terbutryn, propham, alachlor, acifluorfen, bentazon, metolachlor and N,N-dialkyl thiocarbamates such as EPTC, butylate or vernolate. These, as well as other herbicides described, for example, in the *Herbicide Handbook of the Weed Science Society of America*, may be used in combination with a compound or compounds of the invention. Typically such formulations will contain from about 5 to about 95 percent by weight of a compound of this invention.

The herbicidal formulations contemplated herein can be applied by any of several method known to the art. Generally, the formulation will be surface applied as an aqueous spray. Such applications can be carried out by conventional ground equipment, of if desired, the sprays can be aerially applied. Soil incorporation of such surface applied herbicides is accomplished by natural leaching, and is, of course, facilitated by natural rainfall and melting snow. If desired, however, the herbicides can be incorporated into the soil by conventional tillage means.

The compound prepared as described in Examples I was screened for herbicidal efficacy, against a variety of broadleaf and grassy weed species, under controlled laboratory conditions of light, humidity and temperature. A solvent solution of said compound was applied, both preemergence and postemergence, to test flats containing the various weed species, and herbicidal efficacy was determined by visual inspection, periodically after application of the compounds. Herbicidal efficacy was determined on a Numerical Injury Rating scale of from 0 (no injury) to 10 (all plants dead).

The following Table sets forth Numerical Injury Ratings of the compound prepared in Example 1 against a variety of common weed species at application rates of 10 pounds per acre preemergence and 10 pounds per acre postemergence. The Numerical Injury Ratings were determined twenty one days subsequent to application.

| Weed | Pre | Post |
| --- | --- | --- |
| Teaweed | 10 | 10 |
| Jimsonweed | 10 | 10 |
| Wild Mustard | 10 | 10 |
| Coffeeweed | 9 | 10 |
| Velvetleaf | 10 | 10 |
| Tall Morningglory | 9 | 9 |
| Yellow Nutsedge | 4 | 10 |
| Yellow Foxtail | 10 | 10 |
| Large Crabgrass | 9 | — |
| Johnsongrass | 10 | 6 |
| Wild Oats | 10 | 10 |
| Barnyardgrass | 10 | 9 |

Based on said screening test, the compounds of this invention could be used for preemergence or postemergence control of a wide variety of broadleaf and grassy weeds. Typical of the various species of terrestrial vegetative growth that may be controlled, combated, or eliminated are, for example, annuals such as pigweed, lambsquarters, foxtail, crabgrass, wild mustard, field pennycress, ryegrass, goose grass, chickweed, wild oats, velevetleaf, pursiane, barnyardgrass, smartweed, knotweed, cocklebur, kochia, medic, ragweed, hempnettle, spurrey, pondweed, carpetweed, morningglory, ducksalad, cheatgrass, fall panicum, jimsonweed, witchgrass, watergrass, wild turnip, and similar annual grasses and weeds. Biennials that may be controlled include wild barley, campion, burdock, bull thistle, roundleaved mallow, purple star thistle, and the like.

Also controlled by the compounds of this invention are perennials such as quackgrass, Johnsongrass, Canada thistle, curly dock, field chickweed, dandelion, Russian knapweed aster, horsetail ironweed, sesbania, cattail, wintercress, horsenettle, nutsdge, milkweed, sicklepod, and the like.

The compounds of this invention are also useful as aquatic algicides, aquatic plant growth regulators and aquatic herbicides. Thus this invention provides a method for controlling aquatic plant growth by applying an aquatic herbicidally effective amount of a compound of this invention to aquatic plants to be controlled or to the water in which the plants are growing. Typical of the various species of aquatic vegetation which the herein described compounds may be used to control are aquatic algae, such as, for example, *Chlorella vulgaris, Scenedesmus quadricanda, Anacystis nidulans* and the like; aquatic plants, such as, for example, Hydrilla, Coontail, Duckweed, S.Naiad, Eurasion milfoil, Cambomba, Sago pond weed, water hyacinth and the like.

The aquatic plant growth control method of this invention is practiced by adding the active oxadiazolimidazolidinone compound to the water containing the submerged, emergent, ditchbank or floating aquatic plants, or otherwise contacting the plants with the active compounds, for example, by applying the compounds to the sub-aqueous soil in which the aquatic plants are rooted. The compounds may be applied to the water as dusts when admixed with a powdered solid carrier such as bentonite. Fuller's earth, diatomaceous earth, or various mineral silicates, e.g., mica, talc, pyrophyllite, and clays. The compounds may also be mixed with surface-active dispersing agents to form concentrates to facilitate dispersion in water and to improve the wetting properties when used as sprays. If desired, the compounds may be mixed with a powdered solid carrier, together with a surface-active dispersing agent, so that a wettable powder may be obtained which may be applied directly, or which may be shaken with water to make an aqueous dispersion for application in that form. These wettable powder formulations suitably contain from about 25 to about 85 percent by weight of the active ingredient, i.e., an aquatic growth regulating compound coming within the scope of the general formula. The compounds may be dissolved in an oil, such as a hydrocarbon or chlorinated hydrocarbon oil, and the oil solution of the compound dispersed in water with the aid of a surface-active dispersing agent to give a sprayable aqueous dispersion. Such surface active dispersing agents may be anionic, nonionic, or cationic surface-active agents. Such surface-active agents are well-known, and reference is made to Hoffman et al., U.S. Pat. No. 2,614,916, columns 2-4 for detailed examples of the same. The compounds useful in this embodiment of the invention may also be applied by the aerosol method. Solutions for the aerosol treatment may be prepared by dissolving the compound directly in the aerosol carrier, which is a liquid under pressure, but which is a gas at ordinary temperature (e.g. 20° C.) and atmospheric pressure; or, the aerosol solution may be prepared by first dissolving the compound in a less volatile solvent, and then admixing such solution with the highly volatile liquid aerosol carrier.

Further, the compounds useful as aquatic growth regulators can also be applied in an invert emulsion formulation. An invert emulsion formulation is prepared by first making a solution of an aquatic growth regulating compound in heavy oils, such as diesel fuel, inverting oil, and the like, and combining the thus obtained solution with water under high shear stirring. The thick emulsion is placed in the water and sinks to the bottom of the lake, pond, or the like, and the aquatic growth regulator is gradually released to control the growth of the aquatic plants.

The compounds useful as aquatic growth regulators can also be applied as pellets which are prepared from a mixture of about 5% of the active ingredient, about 85% clay, and about 10% water, all percentages being by weight. The mixture is then extruded through a pellet mill using a suitably sized die, e.g., about ⅛ in. diameter. The extruded pellets are about ⅛ in. by 1½ in., and are typically dried to about 8% moisture content.

The method of controlling aquatic plant growth provided by this invention is practiced by adding to the water containing the submerged or floating plants a growth-regulating or herbicidal amount of one of the herein-disclosed compounds, such that a concentration of from about 0.01 to about 10 ppm. of the active compound is attained. A preferred method of aquatic plant growth regulation provided by this invention is directed toward the control of plants such as water hyacinth. Such plants can be controlled by foliar or root application of a compound of this invention at a rate of about 0.01 to about 1.0 pounds per acre (about 0.011 to about 1.1 kg/ha).

The optimum concentration of active compound for any specific aquatic weed control problem varies with the temperature, the species to be controlled, and the shape of the body of water to be treated. At higher water temperatures, less compound is generally required for a given degree of control than is needed at lower temperatures. When used to control algae or aquatic plant growth, the compounds will usually be employed at concentrations of about 0.1 to about 10 ppm. In terms of pounds of compound per acre of water one foot deep, 0.1 to 10 ppm. is equal to about 0.3 to about 30 pounds per acre of water one foot deep.

Although the invention has been described in considerable detail by the foregoing, it is to be understood that many variations may be made therein by those skilled in the art without departing from the spirit and scope thereof as defined by the appended claims.

We claim:

1. A method for controlling the growth of aquatic plants by contacting the plants or the water in which they are growing with an aquatically herbicidally effective amount of compound represented by the formula:

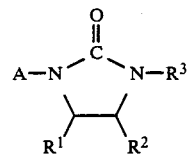

wherein:
A is

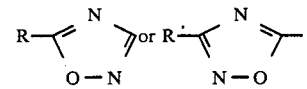

R is alkyl or haloalkyl of up to 6 carbon atoms, cycloalkyl of from 3 to 8 carbon atoms, alkenyl or alkynyl of up to 5 carbon atoms, $-R^4-O-R^5$ $R^4-S-R^5$ wherein $R^4$ is alkylene of up to 6 carbon atoms and $R^5$ is alkyl of up to 6 carbon atoms,

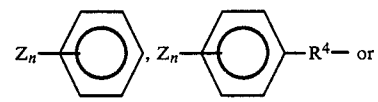

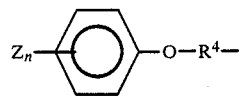

wherein Z is nitro, halogen, trifluoromethyl or $R^5$ and n is 0, 1, 2, or 3;
$R^1$ is hydroxy, halogen,

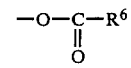

wherein $R^6$ is alkyl or haloalkyl of up to 6 carbon atoms, cycloalkyl of from 3 to 8 carbon atoms, alkenyl or alkynyl of up to 5 carbon atoms or

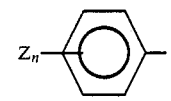

wherein $Z^1$ is nitro, halogen, trifluoromethyl, alkyl or alkoxy of up to 8 carbon atoms and n is 0, 1, 2 or 3 or

wherein $R^7$ and $R^8$ are the same or different and represent hydrogen, alkyl or haloalkyl of up to 6 carbon atoms; or $R_7$ can be

$R^2$ is hydrogen, hydroxy, alkyl, or haloalkyl of up to 4 carbon atoms or allyl; and
$R^3$ is alkyl of up to 3 carbon atoms or allyl.

2. The method of use for the compounds according to claim 1 wherein R and $R^3$ are alkyl, $R^1$ is hydroxy and $R^2$ is a hydrogen or hydroxy.

3. The method of use according to claim 2 wherein said compound is 3-[(5-1,1-dimethylethyl)-1,2,4-oxadiazol-3-yl]-1-methyl-4-hydroxy-2-imidazolidinone.

4. An aquatic herbicide composition containing a compound or mixture of compounds defined in claim 1 and an aquatically acceptable carrier.

* * * * *